(12) United States Patent
Akamine et al.

(10) Patent No.: US 8,444,961 B2
(45) Date of Patent: May 21, 2013

(54) RNA VIRUS INFECTION INHIBITOR, METHOD FOR INHIBITION OF INFECTION BY RNA VIRUS, RNA VIRUS INFECTION-INHIBITING PRODUCT, AND USE AS RNA VIRUS INFECTION INHIBITOR

(75) Inventors: Takayuki Akamine, Shimamoto-cho (JP); Akihiko Fujiwara, Shimamoto-cho (JP); Taro Suzuki, Shimamoto-cho (JP)

(73) Assignee: Sekisui Chemical Co., Ltd., Osaka (JP)

( * ) Notice: Subject to any disclaimer, the term of this patent is extended or adjusted under 35 U.S.C. 154(b) by 0 days.

(21) Appl. No.: 13/378,150

(22) PCT Filed: Jun. 16, 2010

(86) PCT No.: PCT/JP2010/060248
§ 371 (c)(1),
(2), (4) Date: Dec. 14, 2011

(87) PCT Pub. No.: WO2010/147165
PCT Pub. Date: Dec. 23, 2010

(65) Prior Publication Data
US 2012/0093763 A1    Apr. 19, 2012

(30) Foreign Application Priority Data
Jun. 16, 2009   (JP) ................ 2009-143486

(51) Int. Cl.
*A61K 31/74*    (2006.01)
(52) U.S. Cl.
USPC ........................................ 424/78.08
(58) Field of Classification Search
None
See application file for complete search history.

(56) References Cited

U.S. PATENT DOCUMENTS

| | | | | |
|---|---|---|---|---|
| 4,604,404 | A * | 8/1986 | Munson et al. | 514/494 |
| 5,747,053 | A * | 5/1998 | Nashimoto et al. | 424/405 |
| 5,888,527 | A * | 3/1999 | Nashimoto et al. | 424/405 |
| 6,681,765 | B2 * | 1/2004 | Wen | 128/201.25 |
| 6,740,635 | B2 * | 5/2004 | Matthews et al. | 514/3.8 |
| 6,805,857 | B2 * | 10/2004 | Shah | 424/78.27 |
| 7,642,247 | B2 * | 1/2010 | Daifuku et al. | 514/43 |
| 2002/0025919 | A1 * | 2/2002 | Matthews et al. | 514/2 |
| 2003/0203031 | A1 * | 10/2003 | Shah | 424/485 |
| 2004/0127436 | A1 * | 7/2004 | Daifuku et al. | 514/43 |
| 2004/0234955 | A1 * | 11/2004 | Yamaguchi et al. | 435/5 |
| 2006/0246595 | A1 * | 11/2006 | Banks et al. | 436/86 |
| 2007/0142310 | A1 * | 6/2007 | Daifuku et al. | 514/43 |
| 2007/0148124 | A1 | 6/2007 | Labib et al. | |
| 2007/0207973 | A1 * | 9/2007 | Daifuku et al. | 514/43 |
| 2009/0041818 | A1 * | 2/2009 | Otsuki et al. | 424/402 |
| 2009/0320849 | A1 * | 12/2009 | Biedermann | 128/206.28 |
| 2012/0065071 | A1 * | 3/2012 | Li et al. | 504/361 |

FOREIGN PATENT DOCUMENTS

| | | |
|---|---|---|
| EP | 0730462 B1 | 6/2005 |
| EP | 0730462 B1 * | 6/2005 |
| JP | 5-139981 | 6/1993 |
| JP | 6-128877 | 5/1994 |
| JP | 11-507105 | 6/1999 |
| JP | 2005-112748 | 4/2005 |
| JP | 2005-198676 | 7/2005 |
| JP | 2008-115506 | 5/2008 |
| JP | 2011-20993 | 2/2011 |
| JP | 2011-136977 | 7/2011 |
| WO | 98/03572 | 1/1998 |
| WO | 02/45706 | 6/2002 |
| WO | 2008/009651 | 1/2008 |
| WO | WO 2008009651 A1 * | 1/2008 |

OTHER PUBLICATIONS

Antonella Bugatti, Chiara Urbinati, Cosetta Ravelli, Erik De Clercq, Sandra Liekens and Marco Rusnati. Heparin-Mimicking Sulfonic Acid Polymers as Multitarget Inhibitors of Human Immunodeficiency Virus Type 1 Tat and gp120 Proteins. Antimicrob. Agents Chemother. Jul. 2007 vol. 51 No. 7 2337-2345.*

Lourens J.D. Zaneveld, Donald P. Waller, Robert A. Anderson, Calvin Chany II, William F. Rencher, Kenneth Feathergill, Xiao-Hui Diao, Gustavo F. Doncel, Betsy Herold, and Morris Cooper. Efficacy and Safety of a New Vaginal Contraceptive Antimicrobial Formulation Containing High Molecular Weight Poly(Sodium 4-Styrenesulfonate). Biology of Reproduct.*

S Ikeda, J Neyts, S Verma, A Wickramasinghe, P Mohan and E De Clercq. In vitro and in vivo inhibition of ortho- and paramyxovirus infections by a new class of sulfonic acid polymers interacting with virus-cell binding and/or fusion. Antimicrob. Agents Chemother. Feb. 1994 vol. 38 No. 2 256-259.*

Antonella Bugatti, Chiara Urbinati, Cosetta Ravelli, Erik De Clercq, Sandra Liekens and Marco Rusnati. Heparin-Mimicking Sulfonic Acid Polymers as Multitarget Inhibitors of Human Immunodeficiency Virus Type 1 Tat and gp 120 Proteins. Antimicrob. Agents Chemother. Jul. 2007 vol. 51 No. 7 2337-2345.

Lorens J.D. Zaneveld et al. Efficacy and Safety of a New Vaginal Contraceptive Antimicrobial Formulation Containing High Molecular Weight Poly(Sodium 4-Styrenesulfonate). Biology of Reproduction (2002) 66:886-894.

P. Mohan et al., "Sulfonic Acid Polymers as A New Class of Human Immunodeficiency Virus Inhibitors", Antiviral Research, vol. 18, No. 2, pp. 139-150, 1992.

G. T. Tan et al., "Sulfonic Acid Polymers are Potent Inhibitors of HIV-1 Induced Cytopathogenicity and the Reverse Transcriptases of Both HIV-1 and HIV-2", Biochimica et Biophysica Acta, vol. 1181, No. 2, pp. 183-188, 1993.

Japanese Office Action issued Aug. 7, 2012 in corresponding Japanese Application No. 2011-519825.

Extended European Search Report issued Feb. 15, 2013 in corresponding European Patent Application No. 10789539.3.

(Continued)

*Primary Examiner* — Robert A Wax
*Assistant Examiner* — Olga V Tcherkasskaya
(74) *Attorney, Agent, or Firm* — Wenderoth, Lind & Ponack, L.L.P.

(57) ABSTRACT

Disclosed herein is an RNA virus infection inhibitor that is capable of effectively inhibiting humans from being infected with RNA viruses to prevent the occurrence of symptoms or, even when symptoms occur, to relieve the symptoms and is less likely to cause unexpected discoloration or discoloration under normal service conditions. The RNA virus infection inhibitor comprises an RNA virus infection-inhibiting compound comprising a linear polymer having, in its side chain, at least one of substituents having structural formulas represented by general formulas (1) to (3).

10 Claims, No Drawings

OTHER PUBLICATIONS

N. Bourne et al., "Poly(sodium 4-styrene sulfonate): evaluation of a topical microbicide gel against herpes simplex virus type 2 and *Chlamydia trachomatis* infections in mice", European Society of Clinical Microbiology and Infectious Diseases, vol. 9, No. 8, Aug. 2003, XP55052670, pp. 816-822.

S. Garg et al., "Development and Characterization of Bioadhesive Vaginal Films of Sodium Polystyrene Sulfonate (PSS), a Novel Contraceptive Antimicrobial Agent", Pharmaceutical Research, vol. 22, No. 4, Apr. 2005, pp. 584-595, XP19370823.

* cited by examiner

RNA VIRUS INFECTION INHIBITOR, METHOD FOR INHIBITION OF INFECTION BY RNA VIRUS, RNA VIRUS INFECTION-INHIBITING PRODUCT, AND USE AS RNA VIRUS INFECTION INHIBITOR

This application is a U.S. national stage of International Application No. PCT/JP2010/060248 filed Jun. 16, 2010.

TECHNICAL FIELD

The present invention relates to an RNA virus infection inhibitor, a method for inhibition of infection by RNA virus, an RNA virus infection-inhibiting product obtained by treating an RNA virus target object with the RNA virus infection inhibitor, and use as an RNA virus infection inhibitor.

BACKGROUND ART

In recent years, there have been concerns about not only epidemic of seasonal influenza but also human pandemic of highly-pathogenic avian influenza caused by the mutation of avian influenza viruses.

Further, there has also been a concern about a new outbreak of the highly lethal SARS virus. Under the circumstances, the fears of highly-pathogenic RNA viruses are increasing. In order to address such problems, for example, Patent Document 1 discloses an article useful for inactivating viruses upon contact. The article comprises a fabric substrate bearing a coating of immobilized polymer molecules that provides the fabric substrate with nonleachable antiviral activity, wherein the polymer molecules comprise a hydrophilic polymer having pendant antiviral groups comprising a plurality of pendant cationic groups comprising quaternary ammonium groups and a plurality of pendant hydrocarbon groups.

Patent Document 2 discloses an antiviral agent comprising, as an active ingredient, a water-insoluble aromatic hydroxy compound having a phenolic hydroxyl group at least one position. Patent Document 3 discloses an antiviral mask comprising a filter material having at least one layer containing citric acid as hydroxy acid having both a hydroxyl group (—OH) and a carboxyl group (—COOH). Patent Document 4 discloses an antiviral agent for fiber treatment comprising poly-oxyethylene(dimethylimino)ethylene(dimethylimino) ethyl ene dichloride.

However, the quaternary ammonium groups contained in the article disclosed in Patent Document 1 are cationic groups, and therefore a surfactant or the like needs to coexist to allow the polymer to be contained in a fiber such as rayon, which causes a problem that antiviral activity is lowered.

The water-insoluble aromatic hydroxy compound having a phenolic hydroxyl group disclosed in Patent Document 2 has a problem that white fibers are colored when treated therewith or its antiviral activity is not sufficient.

Citric acid used in Patent Document 3 is sensitive to repeated washing, and therefore has a problem that its antiviral activity is lowered by washing. Poly-oxyethylene(dimethylimino)ethylene(dimethylimino)ethyl ene dichloride used in Patent Document 4 has a problem that it is not suitable for use in daily clothes due to the dermal irritancy of a halogen.

Patent Document 5 discloses that antibacterial activity is imparted to fibers by graft polymerization of an acidic group-containing vinyl-based monomer onto the fibers. However, as described in paragraphs (0005) and (0006) in Patent Document 4, various antibacterial compounds have been heretofore developed and many of them have been used for fiber products, but it cannot be said that such antibacterial compounds inhibit viral infection. For this reason, there has been demand for development of viral infection inhibitors excellent in fiber processability.

PRIOR ART DOCUMENTS

Patent Documents

Patent Document 1: JP-T-11-507105
Patent Document 2: JP-A-2005-112748
Patent Document 3: JP-A-2005-198676
Patent Document 4: JP-A-2008-115506
Patent Document 5: JP-A-6-128877

SUMMARY OF THE INVENTION

Problems to be Solved by the Invention

It is therefore an object of the present invention to provide an RNA virus infection inhibitor that is capable of effectively inhibiting humans from being infected with RNA viruses to prevent the occurrence of symptoms or, even when symptoms occur, to relieve the symptoms and is less likely to cause unexpected discoloration or discoloration under normal service conditions, a method for inhibition of infection by RNA virus, an RNA virus infection-inhibiting product obtained by treating an RNA virus target object with the RNA virus infection inhibitor, and use as an RNA virus infection inhibitor.

Means for Solving the Problems

In order to achieve the above object, the present invention is directed to an RNA virus infection inhibitor comprising an RNA virus infection-inhibiting compound comprising a linear polymer having, in its side chain, at least one of substituents having structural formulas represented by the following general formulas (1) to (3):

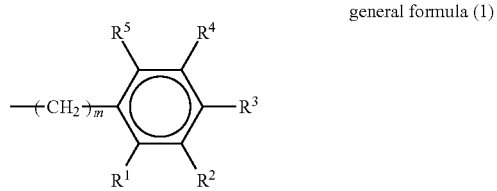

general formula (1)

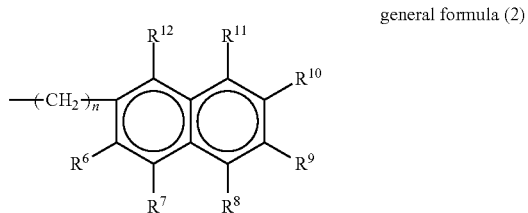

general formula (2)

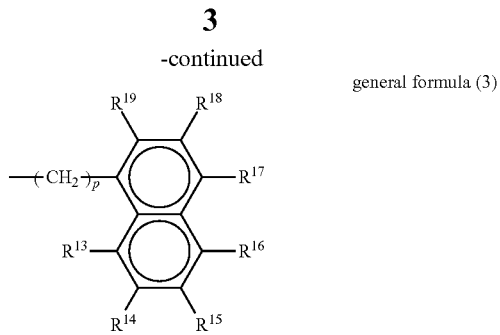

general formula (3)

wherein m, n, and p are each an integer of 0 to 2, $R^1$ to $R^{19}$ are each hydrogen, a carboxy group or a salt or derivative thereof, or a sulfonic acid group or a salt or derivative thereof, and wherein at least one of $R^1$ to $R^5$ is a carboxy group, a sulfonic acid group, or a salt or derivative thereof, at least one of $R^6$ to $R^{12}$ is a carboxy group, a sulfonic acid group, or a salt or derivative thereof, and at least one of $R^{13}$ to $R^{19}$ is a carboxy group, a sulfonic acid group, or a salt or derivative thereof.

Here, the term "RNA virus infection inhibitor" refers to one having a viral infection-inhibiting effect. The term "viral infection-inhibiting effect" refers to the effect of preventing cells from being infected with RNA viruses such as influenza viruses, coronaviruses, and caliciviruses or preventing such RNA viruses from growing in cells after infection. Examples of a method for determining the presence or absence of infection with such viruses include a plaque test and a hemagglutination titer (HAU) test described in "Medical and Pharmaceutical Virology" (first issued in April 1990).

As described above, in the above general formulas (1) to (3), m, n, and p are each an integer of 0 to 2. If m, n, and p are 3 or more, the RNA virus infection-inhibiting compound loses its viral infection-inhibiting effect.

In the above general formula (1), $R^1$ to $R^5$ are each hydrogen (—H), a carboxy group (—COOH) or a salt or derivative thereof, or a sulfonic acid group (—$SO_3H$) or a salt or derivative thereof, but at least one of $R^1$ to $R^5$ needs to be a carboxy group, a sulfonic acid group, or a salt or derivative thereof.

Similarly, in the above general formula (2), $R^6$ to $R^{12}$ are each hydrogen (—H), a carboxy group (—COOH) or a salt or derivative thereof, or a sulfonic acid group (—$SO_3H$) or a salt or derivative thereof, but at least one of $R^6$ to $R^{12}$ needs to be a carboxy group, a sulfonic acid group, or a salt or derivative thereof.

In addition, in the above general formula (3), $R^{13}$ to $R^{19}$ are each hydrogen (—H), a carboxy group (—COOH) or a salt or derivative thereof, or a sulfonic acid group (—$SO_3H$) or a salt or derivative thereof, but at least one of $R^{13}$ to $R^{19}$ needs to be a carboxy group, a sulfonic acid group, or a salt or derivative thereof.

This is because if each of the substituents represented by the above general formulas (1) to (3) does not have a carboxy group, a sulfonic acid group, or a salt or derivative thereof as a substituent, the RNA virus infection-inhibiting compound does not exhibit its viral infection-inhibiting effect.

Examples of the salt of a carboxy group include —COONa and (—COO)$_2$Ca. Examples of the salt of a sulfonic acid group include —$SO_3Na$ and (—$SO_3$)$_2Ca$, and —$SO_3^-NH_4^+$.

Examples of the derivative of a carboxy group include esters of a carboxy group such as —$COOCH_3$ and —$COOC_2H_5$. Examples of the derivative of a sulfonic acid group include esters of a sulfonic acid group such as —$SO_3CH_3$ and —$SO_3C_2H_5$.

In the above general formula (1), the number of carboxy groups, sulfonic acid groups, or salts or derivatives thereof is preferably 1 to 3, more preferably 1. This is because if the number of carboxyl groups, sulfonic acid groups, or salts or derivatives thereof is large, the RNA virus infection-inhibiting compound loses its viral infection-inhibiting effect.

Further, in the above general formula (1), it is preferred that $R^3$ is a carboxy group, a sulfonic acid group, or a salt or derivative thereof and that $R^1$, $R^2$, $R^4$, and $R^5$ are each hydrogen. This is because, in this case, steric hindrance is less likely to occur.

The linear polymer having, in its side chain, at least one of the substituents having structural formulas represented by the general formulas (1) to (3) is not particularly limited. Preferred examples of the linear polymer include vinyl polymers and polyesters. Among them, polystyrene is more preferred. The chemical bond between the linear polymer and the substituents having structural formulas represented by the general formulas (1) to (3) is any chemical bond such as a C—C bond, an ester bond, an ether bond, or an amide bond.

Preferred examples of the RNA virus infection-inhibiting compound comprising the linear polymer having, in its side chain, at least one of the substituents having structural formulas represented by the general formulas (1) to (3) include a polymer containing a styrenesulfonic acid component, a sulfonic acid salt of a polymer containing a styrenesulfonic acid component, a sulfonic acid derivative of a polymer containing a styrenesulfonic acid component, a copolymer containing a styrenesulfonic acid salt component and a styrenesulfonic acid derivative component, a homopolymer of styrenesulfonic acid, a homopolymer of a styrenesulfonic acid salt, a styrene-styrenesulfonic acid salt copolymer, a styrene-styrenesulfonic acid copolymer, a compound obtained by sulfonation of the benzene rings of polystyrene, a sulfonic acid salt of a compound obtained by sulfonation of the benzene rings of polystyrene, a sulfonic acid derivative of a compound obtained by sulfonation of the benzene rings of polystyrene, a compound obtained by sulfonation of the benzene rings of a styrene component-containing polymer, a sulfonic acid salt of a compound obtained by sulfonation of the benzene rings of a styrene component-containing polymer, a sulfonic acid derivative of a compound obtained by sulfonation of the benzene rings of a styrene component-containing polymer, a polymer containing a vinylbenzoic acid component, a carboxy salt of a polymer containing a vinylbenzoic acid component, a carboxy derivative of a polymer containing a vinylbenzoic acid component, a copolymer containing a carboxy salt component of vinylbenzoic acid and a carboxy derivative component of vinylbenzoic acid, a homopolymer of vinylbenzoic acid, a homopolymer of a vinylbenzoic acid salt, a styrene-vinylbenzoic acid salt copolymer, a styrene-vinylbenzoic acid copolymer, a compound obtained by introducing carboxy groups into the benzene rings of polystyrene, a carboxy salt of a compound obtained by introducing carboxyl groups into the benzene rings of polystyrene, a carboxy derivative of a compound obtained by introducing carboxy groups into the benzene rings of polystyrene, a compound obtained by introducing carboxy groups into the benzene rings of a styrene component-containing polymer, a carboxy salt of a compound obtained by introducing carboxy groups into the benzene rings of a styrene component-containing polymer, and a carboxy derivative of a compound obtained by introducing carboxy groups into the benzene rings of a styrene component-containing polymer.

The sulfonic acid salt of a polymer containing a styrenesulfonic acid component is not particularly limited, but is preferably a sulfonic acid sodium salt of a polymer containing a styrenesulfonic acid component, a sulfonic acid calcium salt of a polymer containing a styrenesulfonic acid component, or a sulfonic acid ammonium salt of a polymer containing a styrenesulfonic acid component, more preferably a sulfonic acid sodium salt of a homopolymer of styrenesulfonic acid, particularly preferably a sulfonic acid sodium salt of a homopolymer of p-styrenesulfonic acid, most preferably a homopolymer of sodium p-styrenesulfonate. The derivative of a polymer of styrenesulfonic acid is not particularly limited, but is preferably a polymer of ethyl styrenesulfonate.

Preferred examples of a sulfonic acid salt group contained in the sulfonic acid salt of a compound obtained by sulfonation of the benzene rings of polystyrene include a sulfonic acid sodium salt, a sulfonic acid calcium salt, a sulfonic acid ammonium salt, a sulfonic acid magnesium salt, and a sulfonic acid barium salt. Among them, a sulfonic acid sodium salt is more preferred.

Preferred examples of a sulfonic acid salt group contained in the sulfonic acid salt of a compound obtained by sulfonation of the benzene rings of a styrene component-containing polymer include a sulfonic acid sodium salt, a sulfonic acid calcium salt, a sulfonic acid ammonium salt, a sulfonic acid magnesium salt, and a sulfonic acid barium salt. Among them, a sulfonic acid sodium salt is more preferred.

Examples of a monomer component other than a styrene component contained in the styrene component-containing polymer include alkyl acrylates, alkyl methacrylates, vinyl alkyl ethers, vinyl acetate, ethylene, propylene, butylene, butadiene, diisobutylene, vinyl chloride, vinylidene chloride, 2-vinylnaphthalene, acrylonitrile, acrylic acid, sodium acrylate, methacrylic acid, maleic acid, fumaric acid, maleic anhydride, acrylamide, methacrylamide, diacetoneacrylamide, vinyltoluene, xylenesulfonic acid, vinylpyridine, vinylsulfonic acid, vinyl alcohol, methyl methacrylate, sodium methacrylate, and hydroxyethyl methacrylate.

Sulfonation of the benzene rings of a styrene component-containing polymer or of polystyrene can be performed by a well-known technique such as a method using sulfur trioxide or concentrated sulfuric acid. The sulfonic acid salt of a compound obtained by sulfonation of the benzene rings of a styrene component-containing polymer or of polystyrene can be produced by, for example, sulfonating the benzene rings of a styrene component-containing polymer or of polystyrene and neutralizing a suspension containing the sulfonated compound with an alkaline aqueous solution. Examples of the alkaline aqueous solution include sodium hydroxide and potassium hydroxide.

The RNA virus infection-inhibiting compound is preferably a compound obtained by homopolymerization or copolymerization of a monomer or monomers having at least one of the substituents having structural formulas represented by the general formulas (1) to (3). Examples of such a monomer(s) include p-styrenesulfonic acid, m-styrenesulfonic acid, o-styrenesulfonic acid, sodium p-styrenesulfonate, sodium m-styrenesulfonate, sodium o-styrenesulfonate, calcium p-styrenesulfonate, calcium m-styrenesulfonate, calcium o-styrenesulfonate, ammonium p-styrenesulfonate, ammonium m-styrenesulfonate, ammonium o-styrenesulfonate, ethyl p-styrenesulfonate, ethyl m-styrenesulfonate, ethyl o-styrenesulfonate, 4-vinylbenzoic acid, sodium 4-vinylbenzoate, methyl 4-vinylbenzoate, 4-vinylaniline, aminostyrene hydrochloride, N-acetyl aminostyrene, N-benzoyl aminostyrene, naphthalene sulfonic acid, sodium naphthalene sulfonate, and calcium naphthalene sulfonate. Among them, sodium styrenesulfonate is preferred, and sodium p-styrenesulfonate is more preferred because steric hindrance is less likely to occur in reaction with viruses.

The sulfonic acid salt of a polymer containing a styrenesulfonic acid component can be produced by a well-known method. Examples of such a method include one in which a styrenesulfonic acid salt is radically polymerized and one in which sulfonic acid of a homopolymer of styrenesulfonic acid is neutralized with an alkali such as sodium hydroxide, calcium hydroxide, potassium hydroxide, or ammonium hydroxide.

In the molecule of the sulfonic acid salt of a polymer containing a styrenesulfonic acid component, not all of the sulfonic acid groups need to be in the form of a salt. However, when the ratio of sulfonic acid salt groups is low, there is a fear that the RNA virus infection inhibitor has strong acidity and therefore damages a virus target object that will be described later. For this reason, the ratio is preferably 50 mol % or more, more preferably 70 to 100 mol %, particularly preferably 85 to 100 mol %.

The ratio of sulfonic acid salt groups contained in the molecule of the sulfonic acid salt of a polymer containing a styrenesulfonic acid component is calculated in the following manner. In a case where the sulfonic acid salt of a polymer containing a styrenesulfonic acid component is obtained by polymerization of a monomer containing a styrenesulfonic acid salt, the total number of moles of sulfonic acid groups and derivatives thereof in the monomer used in the polymerization is calculated, and the number of moles of sulfonic acid salt groups is also calculated, and the percentage of the number of moles of sulfonic acid salt groups with respect to the total number of moles is calculated. On the other hand, in a case where the sulfonic acid salt of a homopolymer of styrenesulfonic acid is produced by polymerization of styrenesulfonic acid as a monomer to obtain a homopolymer of styrenesulfonic acid and neutralizing the homopolymer of styrenesulfonic acid with alkali, the number of moles of consumed alkali is measured by neutralization titration, the number of moles of styrenesulfonic acid used in the polymerization is measured, and the percentage of the number of moles of the consumed alkali with respect to the number of moles of styrenesulfonic acid used is calculated.

The weight-average molecular weight of the sulfonic acid salt of a homopolymer of styrenesulfonic acid is preferably 20,000 or higher, more preferably 100,000 or higher, particularly preferably 300,000 or higher. This is because if the weight-average molecular weight of the sulfonic acid salt of a homopolymer of styrenesulfonic acid is low, there is a case where the viral infection-inhibiting effect is lowered. However, if the weight-average molecular weight of the sulfonic acid salt of a homopolymer of styrenesulfonic acid is too high, there is a case where the handleability of the RNA virus infection inhibitor is deteriorated, and therefore the upper limit of the weight-average molecular weight of the sulfonic acid salt of a homopolymer of styrenesulfonic acid is preferably 5,000,000.

It is to be noted that, in the present invention, the weight-average molecular weight of a polymer refers to one measured by size exclusion chromatography using polyethylene oxide as a standard substance. The weight-average molecular weight and Z-average molecular weight of a polymer can be measured, for example, under the following conditions:

Column: (two columns of TSKgel GMPWXL (7.8 mmI.D.×30 cm) manufactured by TOSOH Corporation)
Eluant: (0.2M aqueous sodium sulfate solution: acetonitrile=9:1)
Flow rate: 1 mL/min
Temperature: 40° C.
Detection: UV (210 nm)

Standard polyethylene oxide: (7 types of SE-2, 5, 8, 15, 30, 70, and 150 manufactured by TOSOH Corporation)

The RNA virus infection-inhibiting compound may be a copolymer of a monomer having at least one of the substituents having structural formulas represented by the general formulas (1) to (3) and a monomer copolymerizable therewith. Such a copolymer may be a random copolymer or a block copolymer, but is preferably a block copolymer.

In a case where the RNA virus infection-inhibiting compound is a block copolymer of a monomer having at least one of the substituents having structural formulas represented by the general formulas (1) to (3) and a monomer copolymerizable therewith, the polymerization degree of a block derived from the monomer having at least one of the substituents having structural formulas represented by the general formulas (1) to (3) is preferably 5 to 6000. This is because if the polymerization degree is low, there is a case where the RNA virus infection-inhibiting compound does not exhibit its viral infection-inhibiting effect, and on the other hand, if the polymerization degree is high, there is a case where the handleability of the RNA virus infection inhibitor is deteriorated.

In a case where the RNA virus infection-inhibiting compound is a copolymer of a monomer having at least one of the substituents having structural formulas represented by the general formulas (1) to (3) and a monomer copolymerizable therewith, the amount of a monomer component having at least one of the substituents having structural formulas represented by the general formulas (1) to (3) contained in the copolymer is preferably 5 wt % or more. This is because if the amount of the monomer component contained in the copolymer is low, there is a case where the RNA virus infection-inhibiting compound does not exhibit its viral infection-inhibiting effect.

Examples of the monomer copolymerizable with the monomer having at least one of the substituents having structural formulas represented by the general formulas (1) to (3) include alkyl acrylates, alkyl methacrylates, vinyl alkyl ethers, vinyl acetate, ethylene, propylene, butylene, butadiene, diisobutylene, vinyl chloride, vinylidene chloride, 2-vinylnaphthalene, styrene, acrylonitrile, acrylic acid, sodium acrylate, methacrylic acid, maleic acid, fumaric acid, maleic anhydride, acrylamide, methacrylamide, diacetoneacrylamide, vinyltoluene, xylenesulfonic acid, vinylpyridine, vinylsulfonic acid, vinyl alcohol, methyl methacrylate, sodium methacrylate, and hydroxyethyl methacrylate. From the viewpoints of compatibility with the monomer having at least one of the substituents having structural formulas represented by the general formulas (1) to (3) and of imparting water-insolubility to the RNA virus infection-inhibiting compound, styrene is preferred.

If the weight-average molecular weight of the polymer obtained by homopolymerization or copolymerization of a monomer or monomers having at least one of the substituents having structural formulas represented by the general formulas (1) to (3) and the weight-average molecular weight of the copolymer of a monomer having at least one of the substituents having structural formulas represented by the general formulas (1) to (3) and a monomer copolymerizable therewith are low, there is a case where the RNA virus infection-inhibiting compound does not exhibit its viral infection-inhibiting effect, and on the other hand, if the weight-average molecular weights are high, there is a case where the handleability of the RNA virus infection inhibitor is deteriorated. Therefore, in the case of the polymer obtained by homopolymerization of a monomer having at least one of the substituents having structural formulas represented by the general formulas (1) to (3), the weight-average molecular weight thereof is preferably 20,000 to 5,000,000. In the case of the polymer obtained by copolymerization of monomers having at least one of the substituents having structural formulas represented by the general formulas (1) to (3) or the copolymer of a monomer having at least one of the substituents having structural formulas represented by the general formulas (1) to (3) and a monomer copolymerizable therewith, the weight average molecular weight thereof is preferably 5,000 to 5,000,000, more preferably 5,000 to 2,000,000.

The RNA virus infection-inhibiting compound may be soluble or insoluble in water. In a case where the RNA virus infection inhibitor is used to treat RNA virus target objects, such as clothes and futons, required to have washing resistance, the RNA virus infection-inhibiting compound is preferably insoluble in water. Here, the phrase "insoluble in water" means that the number of grams of the RNA virus infection-inhibiting compound soluble in 100 g of water having a pH of 5 to 9 at 20° C. (hereinafter, referred to as "solubility") is 1 or less, and when the solubility of the RNA virus infection-inhibiting compound is larger than 1, the compound is defined as one soluble in water.

When the RNA virus infection-inhibiting compound is insoluble in water, it is possible to inhibit the disappearance of the RNA virus infection inhibitor due to its dissolution in water even when an RNA virus target object comes into contact with water. This makes it possible to stably maintain the virus infection-inhibiting effect of an RNA virus infection-inhibiting product (which will be described later) over a long period of time.

Examples of a method for imparting water-insolubility to the RNA virus infection-inhibiting compound include: (1) a method in which a curing agent is added to a water-soluble RNA virus infection-inhibiting compound to cross-link the RNA virus infection-inhibiting compound; (2) a method in which a water-soluble RNA virus infection-inhibiting compound is dissolved in water to prepare an aqueous RNA virus infection-inhibiting compound solution, and then the aqueous RNA virus infection-inhibiting compound solution is irradiated with ionizing radiation to cross-link the RNA virus infection-inhibiting compound; (3) a method in which a water-soluble RNA virus infection-inhibiting compound is immobilized onto a carrier; and (4) a method in which a cross-linked polymer having a network structure is produced by suspension polymerization of styrene or naphthalene and divinyl benzene in water and carboxy groups, sulfonic acid groups, or salts or derivatives thereof are introduced into the aromatic rings (benzene rings or naphthalene rings) of the polymer.

In a case where a water-soluble RNA virus infection-inhibiting compound is cross-linked to prepare a reaction mixture of the RNA virus infection-inhibiting compound, the reaction mixture of the RNA virus infection-inhibiting compound contains the water-insoluble cross-linked RNA virus infection-inhibiting compound and the water-soluble RNA virus infection-inhibiting compound. Therefore, the reaction mixture of the RNA virus infection-inhibiting compound is supplied into water to prepare a suspension in which the reaction mixture of the RNA virus infection-inhibiting compound is dispersed. Then, the suspension is preferably stirred at 4 to 25° C. for 1 to 4 hours to elute the water-soluble RNA virus infection-inhibiting compound contained in the reaction mixture of the RNA virus infection-inhibiting compound into the water. It is to be noted that the weight of water into which the reaction mixture of the RNA virus infection-inhibiting compound is supplied is preferably 50 to 200 times the weight of the reaction mixture of the RNA virus infection-inhibiting compound. Then, the water-insoluble RNA virus infection-inhibiting compound is separated from the suspension by a general method such as centrifugal separation. The rotation speed of centrifugal separation is preferably 3,000 to 10,000 rpm. The temperature of the suspension during centrifugal separation is preferably 4 to 25° C.

Examples of the ionizing radiation include α rays, γ rays, β rays, electron rays, and ultraviolet rays. Among them, ultraviolet rays are preferred. The amount of ionizing radiation to which the RNA virus infection-inhibiting compound is exposed is preferably 5 to 2,000 kGy, more preferably 50 to 500 kGy. This is because if the amount of ionizing radiation exposure is small, there is a case where water-insolubility cannot be imparted to the RNA virus infection-inhibiting compound and if the amount of ionizing radiation exposure is large, the production efficiency of the RNA virus infection inhibitor is reduced due to long-time exposure to ionizing radiation.

In a case where the RNA virus infection-inhibiting compound is irradiated with ionizing radiation, the RNA virus infection-inhibiting compound may be directly irradiated with ionizing radiation or may be irradiated with ionizing radiation that has passed through an ionizing radiation-permeable synthetic-resin sheet.

When the aqueous RNA virus infection-inhibiting compound solution is irradiated with ionizing radiation, the amount of the RNA virus infection-inhibiting compound contained in the aqueous RNA virus infection-inhibiting compound solution is preferably 5 wt % or more, more preferably 15 to 30 wt %. This is because if the RNA virus infection-inhibiting compound content is low, there is a case where the cross-linking of the RNA virus infection-inhibiting compound cannot be satisfactorily performed.

The weight-average molecular weight of the water-insoluble RNA virus infection-inhibiting compound obtained by cross-linking the water-soluble RNA virus infection-inhibiting compound by irradiation with ionizing radiation is preferably 5,000 to 5,000,000, more preferably 50,000 to 2,000,000. This is because if the weight-average molecular weight of the water-insoluble RNA virus infection-inhibiting compound is small, there is a case where water-insolubility cannot be sufficiently imparted to the RNA virus infection-inhibiting compound and if the weight-average molecular weight of the water-insoluble RNA virus infection-inhibiting compound is large, the handleability of the RNA virus infection-inhibiting compound is deteriorated.

When the water-soluble RNA virus infection-inhibiting compound is irradiated with ionizing radiation, a cross-linking aid may be used. The cross-linking aid is not particularly limited as long as it can promote the cross-linking of the RNA virus infection-inhibiting compound. Examples of such a cross-linking aid include multi-functional monomers such as neopentyl glycol dimethacrylate and trimethylol propane trimethacrylate and oligomers thereof. The amount of the cross-linking aid contained in the aqueous RNA virus infection-inhibiting compound solution is preferably 1 to 5 wt %.

In a case where the RNA virus infection-inhibiting compound has a sulfonic acid group or a salt or derivative thereof, examples of a method for imparting water-insolubility to the RNA virus infection-inhibiting compound include: one in which part of the RNA virus infection-inhibiting compound is desulfonated; one in which the structure of a sulfonic acid salt moiety is partially modified, one in which the RNA virus infection-inhibiting compound is converted into a poorly-water-soluble salt. It is to be noted that an example of the desulfonation method is one in which the RNA virus infection-inhibiting compound is reacted with water vapor at high temperature, and an example of the method for modifying the structure of a sulfonic acid salt moiety is one in which the RNA virus infection-inhibiting compound is melted in sodium hydroxide and then phenolated.

In a case where the RNA virus infection-inhibiting compound is a copolymer of a monomer having at least one of the substituents having structural formulas represented by the general formulas (1) to (3) and a monomer copolymerizable therewith, a highly-hydrophobic monomer may be selected as the monomer copolymerizable with the monomer having at least one of the substituents having structural formulas represented by the general formulas (1) to (3). In this case, water-insolubility is imparted to the RNA virus infection-inhibiting compound by increasing its highly-hydrophobic monomer content.

The curing agent to be added to the RNA virus infection-inhibiting compound is not particularly limited as long as it can cross-link the RNA virus infection-inhibiting compound. Examples of such a curing agent include amine compounds, compounds synthesized from amine compounds such as polyaminoamide compounds, tertiary amine compounds, imidazole compounds, hydrazide compounds, melamine compounds, acid anhydrides, phenol compounds, heat-latent cation polymerization catalysts, photo-latent cation polymerization initiators, dicyanamide and derivatives thereof, and divinylbenzene. These curing agents may be used singly or in combination of two or more of them.

The amine compounds are not particularly limited, and examples thereof include: aliphatic amines such as ethylene diamine, diethylenetriamine, triethylenetetramine, tetraethylenepentamine, polyoxypropylenediamine, and polyoxypropylenetriamine and derivatives thereof; alicyclic amines such as menthenediamine, isophoronediamine, bis(4-amino-3-methylcyclohexyl)methane, diaminodicyclohexylmethane, bis(aminomethyl)cyclohexane, N-aminoethylpiperazine, and 3,9-bis(3-aminopropyl)2,4,8,10-tetraoxaspiro(5,5)undecane and derivatives thereof; and aromatic amines such as m-xylenediamine, α-(m-aminophenyl)ethylamine, α-(p-aminophenyl)ethylamine, m-phenylenediamine, diaminodiphenylmethane, diaminodiphenylsulfone, and α,α-bis(4-aminophenyl)-p-diisopropylbenzene and derivatives thereof.

The compounds synthesized from the amine compounds are not particularly limited, and examples thereof include: polyaminoamide compounds synthesized from the amine compound and a carboxylic acid compound such as succinic acid, adipic acid, azelaic acid, sebacic acid, dodecanedioic acid, isophthalic acid, terephthalic acid, dihydroisophthalic acid, tetrahydroisophthalic acid, or hexahydroisophthalic acid and derivatives thereof; polyaminoimide compounds synthesized from the amine compound and a maleimide compound such as diaminodiphenylmethanebismaleimide and derivatives thereof; ketimine compounds synthesized from the amine compound and a ketone compound and derivatives thereof; and polyamino compounds synthesized from the amine compound and a compound such as an epoxy compound, urea, thiourea, an aldehyde compound, a phenol compound, or an acrylic compound and derivatives thereof.

The tertiary amine compounds are not particularly limited, and examples thereof include N,N-dimethylpiperazine, pyridine, picoline, benzyldimethylamine, 2-(dimethylaminomethyl)phenol, 2,4,6-tris(dimethylaminomethyl)phenol, 1,8-diazabiscyclo(5,4,0)undecene-1 and derivatives thereof.

The imidazole compounds are not particularly limited, and examples thereof include 2-methylimidazole, 2-ethyl-4-methylimidazole, 2-undecylimidazole, 2-heptadecylimidazole, and 2-phenylimidazole and derivatives thereof.

The hydrazide compounds are not particularly limited, and examples thereof include 1,3-bis(hydrazinocarboethyl)-5-isopropylhydantoin, 7,11-octadecadiene-1,18-dicarbohydrazide, eicosanedioic dihydrazide, and adipic dihydrazide and derivatives thereof.

The melamine compounds are not particularly limited, and examples thereof include 2,4-diamino-6-vinyl-1,3,5-triazine and derivatives thereof.

The acid anhydrides are not particularly limited, and examples thereof include phthalic anhydride, trimellitic anhydride, pyromellitic anhydride, benzophenonetetracarboxylic anhydride, ethyleneglycol bis(anhydrotrimellitate), glycerol tris(anhydrotrimellitate), methyltetrahydrophthalic anhydride, tetrahydrophthalic anhydride, nadic anhydride, methyl nadic anhydride, trialkyltetrahydrophthalic anhydrides, hexahydrophthalic anhydride, methylhexahydrophthalic anhydride, 5-(2,5-dioxotetrahydrofuryl)-3-methyl-3-cyclohexene-1,2-dicarboxylic anhydride, trialkyltetrahydrophthalic anhydride-maleic anhydride adducts, dodecenyl succinic anhydride, polyazelaic anhydride, polydodecanedioic anhydride, and chlorendic anhydride and derivatives thereof.

The phenol compounds are not particularly limited, and examples thereof include phenol novolac, o-cresol novolac, p-cresol novolac, t-butylphenol novolac, and dicyclopentadiene cresol and derivatives thereof.

The heat-latent cation polymerization catalysts are not particularly limited, and examples thereof include: ionic heat-latent cation polymerization catalysts such as benzylsulfonium salts, benzylammonium salts, benzylpyridinium salts, and benzylphosphonium salts having a counter anion such as antimony hexafluoride, phosphorus hexafluoride, or boron tetrafluoride; and non-ionic heat-latent cation polymerization catalysts such as N-benzylphthalimide and aromatic sulfonic acid esters.

The photo-latent cation polymerization initiators are not particularly limited, and examples thereof include: ionic photo-latent cation polymerization initiators such as onium salts (e.g., aromatic diazonium salts, aromatic halonium salts, and aromatic sulfonium salts having a counter anion such as antimony hexafluoride, phosphorus hexafluoride, or a boron tetrafluoride) and organic metal complexes (e.g., iron-allene complexes, titanocene complexes, and arylsilanol-aluminum complexes); and non-ionic photo-latent cation polymerization initiators such as nitrobenzyl esters, sulfonic acid derivatives, phosphoric acid esters, phenolsulfonic acid esters, diazonaphthoquinone, N-hydroxyimidosulfonate.

A carrier on which the RNA virus infection-inhibiting compound is to be immobilized is not particularly limited, and examples thereof include: inorganic carriers such as talc, bentonite, clay, kaoline, diatomite, silica, vermiculite, and perlite; and organic polymeric carriers such as polyethylene and polypropylene.

The form of the organic polymeric carrier is not particularly limited, and examples thereof include a microparticulate form, a fiber form, a sheet form, a film form, or a foam. In a case where the RNA virus infection-inhibiting compound is supported on a foam, the RNA virus infection-inhibiting compound may be supported on a foamable molded article that is a raw material of the foam before foaming or may be supported on the foam after foaming.

A method for immobilizing the RNA virus infection-inhibiting compound on the carrier is not particularly limited, and examples thereof include one in which the RNA virus infection-inhibiting compound is adsorbed to the carrier and one in which the RNA virus infection-inhibiting compound is immobilized on the carrier by chemical bonding such as grafting or bonding using a binder.

The RNA virus infection inhibitor according to the present invention may be mixed with a pharmaceutical adjuvant such as a dispersant, an emulsifier, an antioxidant, a UV absorber, or a migration inhibitor as long as its viral infection-inhibiting effect is not inhibited. Further, the RNA virus infection inhibitor according to the present invention may contain a miticide, a bactericide, a fungicide, or a deodorant.

The migration inhibitor is not particularly limited, and examples thereof include salts such as calcium chloride, water-soluble cation compounds, polyvinyl pyrrolidone, polyvinyl pyridine betaine, and polyamine-N-oxide polymers.

Hereinbelow, the usage of the RNA virus infection inhibitor will be described. The RNA virus infection inhibitor may be used in a general form such as spray form, aerosol form, smoke form, thermal-transpiration form, or mixed form with a matrix.

The RNA virus infection inhibitor can be used in spray form by dissolving or dispersing it in a solvent to prepare an RNA virus infection inhibitor solution and adding a water-soluble chemical, an oil solution, an emulsion, or a suspension agent to the RNA virus infection inhibitor solution. It is to be noted that the term "spray form" refers to the type of usage of the RNA virus infection inhibitor allowed by spraying the RNA virus infection inhibitor in mist form through the application of pressure to the RNA virus infection inhibitor solution under normal pressure.

Examples of the solvent include water (preferably, ion-exchange water), alcohols (e.g., methyl alcohol, ethyl alcohol, propyl alcohol), hydrocarbons (e.g., toluene, xylene, methyl naphthalene, kerosene, cyclohexane), ethers (e.g., diethyl ether, tetrahydrofuran, dioxane), ketones (e.g., acetone, methyl ethyl ketone), amides (e.g., N,N-dimethylformamide).

The RNA virus infection inhibitor can be used in aerosol form by adding a solid carrier (e.g., talc, bentonite, clay, kaoline, diatomite, silica, vermiculite, perlite) to the spray-form RNA virus infection inhibitor.

Here, the term "aerosol form" refers to the type of usage of the RNA virus infection inhibitor allowed by charging the RNA virus infection inhibitor solution in a container together with a compressed propellant and spraying the RNA virus infection inhibitor in mist form by the pressure of the propellant. Examples of the propellant include nitrogen, carbon dioxide, dimethyl ether, and LPG.

The RNA virus infection inhibitor can be used in smoke form by adding, to the spray-form RNA virus infection inhibitor, an oxygen-supplying agent (e.g., potassium perchlorate, potassium nitrate, potassium chlorate), a combustion agent (e.g., saccharide, starch), a heat generation adjuster (e.g., guanidine nitrate, nitroguanidine, guanylurea phosphate), or an aid for decomposing an oxygen-supplying agent (e.g., potassium chloride, copper oxide, chromium oxide, iron oxide, activated carbon). It is to be noted that the term "smoke form" refers to the type of usage of the RNA virus infection inhibitor allowed by forming the RNA virus infection inhibitor into micro particles like smoke and dispersing them.

The matrix to be mixed with the RNA virus infection inhibitor is not particularly limited as long as it does not denature the RNA virus infection inhibitor. Examples of such a matrix include polysaccharides and salts thereof, dextrin, gelatin, higher alcohols, oils and fats, higher fatty acids such as stearic acid, paraffins, liquid paraffins, white Vaseline, hydrocarbon gel ointments, polyethylene glycol, polyvinyl alcohol, sodium polyacrylate, and various paints.

The RNA virus infection inhibitor may be supplied to an article by spraying, applying, or fixing it onto the article or dispersing it in the article depending on its usage to prepare an RNA virus infection-inhibiting product capable of generally inhibiting humans from being infected with viruses present on the article. The article is an article where viruses are present or may be present in future, and infection in humans caused by the viruses should be prevented (hereinafter, referred to as an "RNA virus target object"), such as an article for daily use. The RNA virus infection inhibitors may be used singly or in combination of two or more of them. The RNA virus infection inhibitor has excellent stability when prepared as a suspension by mixing the above-described RNA virus infection inhibitor solution with a suspension agent, and therefore the RNA virus infection inhibitor is preferably prepared as a suspension and sprayed onto the RNA virus target object. An example of a method for chemically or physically fixing the RNA virus infection inhibitor to the RNA virus target object is one in which the RNA virus infection-inhibiting compound is chemically bonded or physically fixed to fibers (which will be described later).

Examples of the RNA virus target object include articles for daily use serving as incubators of viruses in living space. Examples of such articles for daily use include tatami mats, carpets, furniture (e.g., sofas, foams inside sofas, ulholstered chairs, and tables), bedclothes (e.g., beds, futons, filling materials for futons, down used in down quilts, sheets, mattresses, cushions, and foams constituting them), articles used inside vehicles such as cars, airplanes and ships, and interior parts of vehicles (e.g., seats, child restraint systems, and foams constituting them), kitchenware, baby goods, interior materials for buildings (e.g., wall papers and floor materials), fiber products (e.g., curtains, towels, clothes, and stuffed toys), filters such as screen doors, screen doors, interior materials for buildings, drugs, quasi drugs, and cosmetics.

Particularly, the RNA virus infection inhibitor according to the present invention hardly causes unexpected coloring or discoloration in our daily living environment, and is therefore suitable for applications that need to prevent color fading or discoloration due to light such as interior materials for buildings, articles used inside vehicles, interior parts for vehicles, filters, and fiber products.

The filters are ones having the ability to perform separation, filtration, and removal of foreign matter. Examples of such a filter include filters used in air purifiers, air conditioners, vacuum cleaners, and exhaust fans, masks, shoji doors, and screen doors or mosquito nets that prevent the entry of insects.

The drugs, quasi drugs, and cosmetics are not particularly limited, and examples thereof include external medicines for skin, nasal sprays, eye drops, shampoos, bath salts, hairdressings, foundations, and face washing products.

The interior materials for buildings are not particularly limited, and examples thereof include floor materials, wall papers, ceiling materials, paints, doorknobs, switches, switch covers, and waxes.

The fiber products are not particularly limited, and examples thereof include bedclothes, carpets, curtains, towels, clothes, and stuffed toys.

The articles used inside vehicles and the interior parts for vehicles are not particularly limited, and examples thereof include seats, child restraint systems, seat belts, car mats, seat covers, doors, ceiling materials, floor mats, door trims, instrument panels, consoles, glove boxes, straps, and handrails. It is to be noted that the RNA virus infection inhibitor is allowed to be contained in fibers used for seats and door trims by the above-described method, and is allowed to be contained in molded articles such as doors, instrument panels, and consoles by coating these molded articles with paints containing the RNA virus infection inhibitor or by previously kneading the RNA virus infection inhibitor into synthetic resins.

The amount of the RNA virus infection inhibitor according to the present invention used in the RNA virus target object is preferably 0.001 to 100 parts by weight, more preferably 0.01 to 50 parts by weight, particularly preferably 0.02 to 30 parts by weight, most preferably 0.02 to 20 parts by weight with respect to 100 parts by weight of the RNA virus target object. This is because if the amount of the RNA virus infection inhibitor used in the RNA virus target object is low, there is a case where the RNA virus infection inhibitor does not exhibit its virus infection-inhibiting effect, and if the amount of the RNA virus infection inhibitor used in the RNA virus target object is large, there is a case where the RNA virus target object is damaged.

Examples of RNA viruses targeted by the RNA virus infection inhibitor according to the present invention include: viruses belonging to the family Reoviridae such as mammalian orthoreovirus and Colorado tick fever virus; viruses belonging to the family Parmyxoviridae such as human parainfluenza viruses 1 and 3, morbillivirus, mumps virus, human parainfluenza viruses 2 and 4, Hendra virus, Nipah virus, and human RS (Respiratory syncytial) virus; viruses belonging to the family Rhabdoviridae such as rabies virus and vesicular stomatitis virus; viruses belonging to the family Filoviridae such as marburg virus, Zaire ebolavirus, and Sudan ebolavirus; viruses belonging to the family Bornaviridae such as Borna disease virus; viruses belonging to the family Orthomyxoviridae such as influenza A virus, influenza B virus, and influenza C virus; viruses belonging to the family Bunyaviridae such as La Crosse virus, Rift Valley fever virus, Crimean-Congo hemorrhagic fever virus, Hantaan virus, and Sin Nombre virus; viruses belonging to the family Arenaviridae such as Lassa virus, lymphocytic choriomeningitis virus, and Junin virus; viruses belonging to the family Picornaviridae such as poliovirus, Coxsackie A virus, Coxsackie B virus, Echo virus, enterovirus, human rhinovirus, hepatitis A virus, and human parechoviruses 1 and 2; viruses belonging to the family Caliciviridae such as Norwalk virus and Sapporo virus; viruses belonging to the family Astroviridae such as human astrovirus; viruses belonging to the family Coronaviridae such as human coronavirus and SARS-associated coronavirus; viruses belonging to the family Flaviviridae such as Japanese encephalitis virus, yellow fever virus, dengue virus, tick-borne encephalitis virus, West Nile virus, and hepatitis C virus; viruses belonging to the family Togaviridae such as Eastern equine encephalitis virus Chikungunya virus, and Rubella virus, and viruses belonging to the family Retroviridae such as human T-cell leukemia virus and human immunodeficiency virus-1.

According to the above-described usage of the RNA virus infection inhibitor, it is possible to generally inhibit humans from being infected with viruses that are present on the RNA virus target object or may be present on the RNA virus target object in future by supplying the RNA virus infection inhibitor to the RNA virus target object when necessary.

The RNA virus infection inhibitor may be allowed to be contained in a fiber to provide a viral infection-inhibiting fiber, that is, the viral infection-inhibiting effect may be imparted to a fiber itself. The above-described articles for daily use may be produced using such viral infection-inhibiting fibers, which makes it possible to impart the viral infection-inhibiting effect to the articles for daily use in advance.

Examples of a method for allowing the RNA virus infection inhibitor to be contained in fibers include one in which the RNA virus infection inhibitor is chemically bonded or physically fixed to fibers and one in which the RNA virus infection inhibitor is allowed to be contained in fibers. The fibers are not particularly limited as long as they can contain the RNA virus infection inhibitor, and examples thereof include: synthetic fibers such as polyester fibers, nylon fibers, acrylic fibers, and polyolefin-based fibers; semisynthetic fibers such as acetate fibers; regenerated fibers such as cupra and rayon; natural fibers such as cotton, hemp, wool, and silk; composite fibers thereof; and cotton blending.

An example of the method for chemically bonding the RNA virus infection inhibitor to fibers is one in which the RNA virus infection inhibitor is chemically bonded to fibers by grafting reaction. The grafting reaction is not particularly limited, and examples thereof include: (1) a graft polymerization method in which a polymerization initiation point is formed on a main polymer that is to be a fiber and the RNA virus infection inhibitor is grafted thereon as a branch polymer; and (2) a polymer reaction method in which the RNA virus infection inhibitor is chemically bonded to fibers by polymer reaction.

Examples of the graft polymerization method include: (1) one in which radicals are generated and polymerized by chain transfer reaction to the fibers; (2) one in which an oxidation-reduction (redox) system is formed by the action of a reducing substance such as an alcohol, thiol, or amine on a ceric salt or silver sulfate and free radicals are generated on the fibers and polymerized; (3) one in which the fibers are irradiated with γ rays or accelerated electron rays in a state where the fibers and a monomer as a raw material of the RNA virus infection-inhibiting compound are present together; (4) one in which only the fibers are irradiated with γ rays or accelerated electron rays and then a monomer as a raw material of the RNA virus infection-inhibiting compound is added thereto to perform polymerization; (5) one in which a polymer constituting the fibers is oxidized to introduce a peroxy group or to introduce a diazo group from an amino group on a side chain and polymerization is performed using such a group as a polymerization initiation point; and (6) one utilizing a polymerization initiation reaction of epoxy, lactam, or a polar vinyl monomer performed by the action of an active group on a side chain such as a hydroxyl group, an amino group, or a carboxyl group.

Specific graft polymerization methods are listed below: (a) one in which free radicals are generated by triturating cellulose in a monomer as a raw material of the RNA virus infection-inhibiting compound to perform graft polymerization; (b) one in which graft polymerization is performed by using a monomer as a raw material of the RNA virus infection-inhibiting compound and a cellulose derivative (e.g., mercaptoethylcellulose) as fibers having a group susceptible to chain transfer; (c) one in which radicals are generated by oxidizing ozone or a peroxide to perform graft polymerization; (d) one in which a double bond of allyl ether, vinyl ether, or methacrylic ester is introduced into the side chain of cellulose to perform graft polymerization; (e) one in which fibers are irradiated with ultraviolet rays using sodium anthraquinone-2,7-disulfonate as a photosensitizer to perform graft polymerization; (f) one in which fibers are wound around a cathode and a monomer as a raw material of the RNA virus infection-inhibiting compound is added to dilute sulfuric acid, and an external voltage is applied to electrochemically perform graft polymerization.

In view of the fact that the graft polymerization is intended for fibers, the following methods are preferred: (g) one in which fibers coated with glycidyl methacrylate (GMA) and benzoyl peroxide are heated in the solution of a monomer as a raw material of the RNA virus infection-inhibiting compound to perform graft polymerization; and (h) one in which a monomer as a raw material of the RNA virus infection-inhibiting compound is added to a liquid obtained by dispersing benzoyl peroxide, a surfactant (nonionic surfactant or anionic surfactant), and monochloro benzene in water and fibers such as polyester-based fibers are immersed in the liquid and heated to perform graft polymerization.

Examples of the polymer reaction method include general methods such as (1) chain transfer reaction, oxidation reaction, or substitution reaction to C—H, (2) addition reaction or oxidation reaction to a double bond, (3) esterification, etherification, or acetalization of a hydroxyl group, substitution reaction, addition reaction, or hydrolytic reaction to an ester group or an amide group, or substitution reaction or elimination reaction to a halogen group, and (4) substitution reaction (halogenation, nitration, sulfonation, or chloromethyaltion) to an aromatic ring.

Hereinbelow, the method for physically fixing the RNA virus infection inhibitor to fibers will be described. Examples of the method for physically fixing the RNA virus infection inhibitor to fibers include: (1) one in which the RNA virus infection inhibitor is dissolved or dispersed in a solvent to prepare an RNA virus infection inhibitor solution and fibers are immersed in the RNA virus infection inhibitor solution to impregnate the fibers with the RNA virus infection inhibitor solution; (2) one in which the RNA virus infection inhibitor solution is applied onto the surface of fibers; (3) one in which fibers are immersed in a binder in which the RNA virus infection inhibitor is dissolved or dispersed to fix the RNA virus infection inhibitor to the fibers by the binder; and (4) one in which a binder in which the RNA virus infection inhibitor is dissolved or dispersed is applied onto the surface of fibers to fix the RNA virus infection inhibitor to the fibers by the binder. It is to be noted that in the above-described methods (1) and (2), the RNA virus infection inhibitor solution may contain a binder that will be described below.

The solvent is not particularly limited, and examples thereof include: water; alcohols such as methyl alcohol, ethyl alcohol, and propyl alcohol; hydrocarbons such as toluene, xylene, methyl naphthalene, kerosene, and cyclohexane; ethers such as diethyl ether, tetrahydrofuran, and dioxane; ketones such as acetone and methyl ethyl ketone; and amides such as N,N-dimethylformamide.

The binder is not particularly limited as long as it can fix the RNA virus infection inhibitor to the surface of fibers. Examples of such a binder made of a synthetic resin include: urethane-based resins such as one-component urethane resins and two-component urethane resins; acrylic resins; urethane acrylate resins; polyester resins; unsaturated polyester resins; alkyd resins; vinyl acetate resins; vinyl chloride resins; epoxy resins; and epoxy acrylate resins. Among them, urethane-based resins are preferred.

The method for allowing the RNA virus infection inhibitor to be contained in fibers has been described above with reference to a case where the RNA virus infection inhibitor is chemically bonded or physically fixed to fibers separately produced, but fibers may be produced by spinning a fiber material having the RNA virus infection inhibitor chemically bonded thereto or by spinning a spinning solution prepared by adding the RNA virus infection inhibitor to a fiber material.

A method for preparing a fiber material having the RNA virus infection inhibitor chemically bonded thereto is not particularly limited, and an example thereof is a method in which a monomer having at least one of the substituents having structural formulas represented by the general formulas (1) to (3) is copolymerized with a monomer as a common fiber material to prepare a fiber material.

A method for producing fibers by spinning a spinning solution prepared by adding the RNA virus infection inhibitor to a fiber material is not particularly limited, and an example thereof is a method in which a spinning solution is prepared by adding the RNA virus infection inhibitor, which is, if necessary, dissolved or suspended in an aqueous sodium hydroxide solution, to a solution containing cellulose dissolved therein and the spinning solution is extruded into a regeneration bath to produce fibers containing the RNA virus infection inhibitor by coagulation and regeneration.

Examples of the solution containing cellulose dissolved therein include viscose and a solution containing cellulose dissolved in cuprammonium. Viscose is produced, for example, in the following manner. Dissolving pulp for rayon (containing 92 to 93 wt % of α-cellulose) produced from needle-leaved trees or broad-leaved trees by a sulfite process or a sulfate process is prepared as a cellulose material, and the cellulose material is reacted with an aqueous sodium hydroxide solution to produce alkali cellulose. Then, the alkali cellulose is aged by allowing it to stand at 25 to 35° C. for 24 to 72 hours and the degree of polymerization of cellulose is reduced so that the cellulose has a viscosity suitable for spinning. Then, carbon bisulfide is added to the alkali cellulose to form sodium cellulose xanthate to produce viscose.

The solution containing cellulose dissolved in cuprammonium is produced, for example, in the following manner. As a cellulose material, purified cotton linters or purified wood pulp are/is used. Particularly, linters containing 99 wt % or more of α-cellulose are preferred. Ammonia water is reacted with a cupric sulfate solution at room temperature to form a basic cupric sulfate, and then sodium hydroxide is added to prepare cuprammonium. Then, the cellulose material is added to the cuprammonium to produce a solution containing cellulose dissolved in cuprammonium.

The amount of the RNA virus infection inhibitor to be added to the solution containing cellulose dissolved therein is preferably 0.1 to 50 parts by weight, more preferably 1 to 20 parts by weight with respect to 100 parts by weight of the cellulose. This is because if the amount of the RNA virus infection inhibitor to be added is small, there is a case where the viral infection-inhibiting effect of the RNA virus infection inhibitor is lowered, and on the other hand, if the amount of the RNA virus infection inhibitor to be added is large, there is a case where the strength of fibers is reduced and therefore problems occur in practical use.

The thus obtained spinning solution is extruded into a regeneration bath to obtain fibers containing the RNA virus infection inhibitor by coagulation and regeneration. More specifically, in a case where viscose is used as the solution containing cellulose dissolved therein, the viscose contained in the spinning solution is matured by a well-known method, and then the spinning solution is supplied to a spinning machine and extruded into a regeneration bath through a spinneret to obtain fibers containing the RNA virus infection inhibitor by coagulation and regeneration. It is to be noted that the regeneration bath generally contains 8 to 12 wt % of sulfuric acid, 15 to 40 wt % of sodium sulfate, and 0 to 2 wt % of zinc sulfate.

On the other hand, in a case where a solution containing cellulose dissolved in cuprammonium is used as the solution containing cellulose dissolved therein, the viscosity of the spinning solution is adjusted if necessary by adjusting a cellulose concentration, a copper concentration, and an ammonia concentration by dilution with ammonia water, and the spinning solution is filtered using a wire net and defoamed. Then, the spinning solution is spun by stretch spinning to obtain fibers containing the RNA virus infection inhibitor. More specifically, the spinning solution is extruded into hot water at 30 to 45° C. through a spinneret having relatively-large holes with a diameter of 0.5 to 1.0 mm and coagulated to obtain threads, the threads are stretched several hundred times their original length by the flow of water while passing through a funnel, and the threads are passed through a sulfuric acid bath to remove copper and regenerate cellulose to obtain fibers containing the RNA virus infection inhibitor.

Effects of the Invention

Since the RNA virus infection inhibitor according to the present invention contains the RNA virus infection-inhibiting compound comprising a linear polymer having, in its side chain, at least one of the substituents having structural formulas represented by the general formulas (1) to (3), it is possible to generally inhibit humans from being infected with viruses and therefore to prevent the occurrence of symptoms or, even when symptoms occur, to relieve the symptoms.

Further, the RNA virus infection inhibitor according to the present invention is less likely to cause unexpected discoloration or discoloration under normal service conditions, and is therefore suitable for use in various articles for daily use.

MODE FOR CARRYING OUT THE INVENTION

Hereinbelow, embodiments of the present invention will be described in more detail with reference to the following examples, but the present invention is not limited to these examples.

Example 1

20 parts by weight of an aqueous solution of a sodium p-styrene sulfonate homopolymer, the homopolymer being an RNA virus infection-inhibiting compound (manufactured by Tosoh Organic Chemical Co., Ltd. under the trade name of "PS-1", sodium p-styrene sulfonate homopolymer content: 20 wt %, weight-average molecular weight (Mw): 25,000, Z average molecular weight (Mz): 49,000), was added to 80 parts by weight of phosphate-buffered saline (hereinafter, referred to as "PBS"), and then they were uniformly mixed to obtain an RNA virus infection inhibitor solution. It is to be noted that the sodium p-styrene sulfonate homopolymer was water-soluble. The ratio of sulfonic acid groups in sodium salt form contained in the sodium p-styrene sulfonate homopolymer was 100 mol %.

Example 2

An RNA virus infection inhibitor solution was obtained in the same manner as in Example 1 except that 20 parts by weight of an aqueous solution of a sodium p-styrene sulfonate homopolymer, the homopolymer being an RNA virus infection-inhibiting compound (manufactured by Tosoh Organic Chemical Co., Ltd. under the trade name of "PS-50", sodium p-styrene sulfonate homopolymer content: 20 wt %, weight-average molecular weight (Mw): 390,000, Z average molecular weight (Mz): 618,000), was used. It is to be noted that the sodium p-styrene sulfonate homopolymer was water-soluble. The ratio of sulfonic acid groups in sodium salt form contained in the sodium p-styrene sulfonate homopolymer was 100 mol %.

Example 3

An RNA virus infection inhibitor solution was obtained in the same manner as in Example 1 except that 20 parts by weight of an aqueous solution of a sodium p-styrene sulfonate homopolymer, the homopolymer being an RNA virus infection-inhibiting compound (manufactured by Tosoh Organic Chemical Co., Ltd. under the trade name of "PS-100", sodium p-styrene sulfonate homopolymer content: 20 wt %, weight-average molecular weight (Mw): 529,000, Z average molecular weight (Mz): 758,000), was used. It is to be noted that the sodium p-styrene sulfonate homopolymer was water-soluble. The ratio of sulfonic acid groups in sodium salt from contained in the sodium p-styrene sulfonate homopolymer was 100 mol %.

Example 4

An RNA virus infection inhibitor solution was obtained in the same manner as in Example 1 except that 20 parts by weight of an aqueous solution of a sodium p-styrene sulfonate-styrene random copolymer, the copolymer being an RNA virus infection-inhibiting compound (manufactured by Tosoh Organic Chemical Co., Ltd. under the trade name of "ST-5005", sodium p-styrene sulfonate units: 50 wt %, styrene units: 50 wt %, sodium p-styrene sulfonate-styrene random copolymer content: 20 wt %, weight-average molecular weight (Mw): 22,000), was used. It is to be noted that the sodium p-styrene sulfonate-styrene random copolymer was water-soluble. The ratio of sulfonic acid groups in sodium salt form contained in the sodium p-styrene sulfonate-styrene random copolymer was 100 mol %.

Example 5

An RNA virus infection inhibitor solution was obtained in the same manner as in Example 1 except that 40 parts by weight of an aqueous solution of a sodium p-styrene sulfonate-styrene random copolymer, the copolymer being an RNA virus infection-inhibiting compound (manufactured by Tosoh Organic Chemical Co., Ltd. under the trade name of "ST-5008", sodium p-styrene sulfonate units: 50 wt %, styrene units: 50 wt %, sodium p-styrene sulfonate-styrene random copolymer content: 20 wt %, weight-average molecular weight (Mw): 6,000), was used. It is to be noted that the sodium p-styrene sulfonate-styrene random copolymer was water-soluble. The ratio of sulfonic acid groups in sodium salt form contained in the sodium p-styrene sulfonate-styrene random copolymer was 100 mol %.

Example 6

An RNA virus infection inhibitor solution was obtained in the same manner as in Example 1 except that 20 parts by weight of an aqueous solution of a sodium p-styrene sulfonate-sodium methacrylate random copolymer, the copolymer being an RNA virus infection-inhibiting compound (manufactured by Tosoh Organic Chemical Co., Ltd. under the trade name of "MA-2005", sodium p-styrene sulfonate units: 50 wt %, sodium methacrylate units: 50 wt %, sodium p-styrene sulfonate-sodium methacrylate random copolymer content: 20 wt %, weight-average molecular weight (Mw): 3,900), was used. It is to be noted that the sodium p-styrene sulfonate-sodium methacrylate random copolymer was water-soluble. The ratio of sulfonic acid groups in sodium salt form contained in the sodium p-styrene sulfonate-sodium methacrylate random copolymer was 100 mol %.

Example 7

An RNA virus infection inhibitor containing, as an RNA virus infection-inhibiting compound, a sulfonic acid sodium salt of a compound obtained by sulfonation of a styrene-maleic acid copolymer (manufactured by Akzo Nobel under the trade name of "VERSA-TL3", styrene units: 75 wt %, maleic acid units: 25 wt %, ratio of sulfonated styrene units; 99 mol % or more, weight-average molecular weight (Mw): 20,000) was obtained. It is to be noted that the sulfonic acid sodium salt of a compound obtained by sulfonation of a styrenesulfonic acid-maleic acid copolymer was water-soluble.

Example 8

An RNA virus infection inhibitor solution was obtained in the same manner as in Example 1 except that 20 parts by weight of an aqueous solution of a sodium p-styrene sulfonate-2-hydroxyethyl methacrylate random copolymer, the copolymer being an RNA virus infection-inhibiting compound (manufactured by Tosoh Organic Chemical Co., Ltd. under the trade name of "HM-5030", sodium p-styrene sulfonate units: 50 wt %, 2-hydroxyethyl methacrylate units: 50 wt %, sodium p-styrene sulfonate-2-hydroxyethyl methacrylate random copolymer content: 20 wt %, weight-average molecular weight (Mw): 300,000), was used. It is to be noted that the sodium p-styrene sulfonate-2-hydroxyethyl methacrylate random copolymer was water-soluble. The ratio of sulfonic acid groups in sodium salt form contained in the sodium p-styrene sulfonate-2-hydroxyethyl methacrylate random copolymer was 100 mol %.

Examples 9 to 13

An aqueous solution of a water-soluble sodium p-styrene sulfonate homopolymer, the homopolymer being an RNA virus infection-inhibiting compound (manufactured by Tosoh Organic Chemical Co., Ltd. under the trade name of "PS-100", sodium p-styrene sulfonate homopolymer content: 22 wt %, weight-average molecular weight (Mw): 529,000, Z average molecular weight (Mz): 758,000), was supplied into a glass Petri dish so as to have a thickness shown in Table 2, and was irradiated with electron rays at a dose shown in Table 2 to cross-link the sodium p-styrene sulfonate homopolymer. The thus obtained reaction mixture of the sodium p-styrene sulfonate homopolymer gelled.

The reaction mixture of the sodium p-styrene sulfonate homopolymer was mixed with water having a weight 100 times the weight of the reaction mixture to prepare a suspension, and the suspension was allowed to stand at 25° C. for 1 hour under stirring to extract the water-soluble sodium p-styrene sulfonate homopolymer contained in the reaction mixture of the sodium p-styrene sulfonate homopolymer into the water.

Then, the suspension was centrifuged by a centrifugal separator at 8,000 rpm at 15° C. for 3 minutes. The above-described process was repeated three times to separate the cross-linked sodium p-styrene sulfonate homopolymer from the reaction mixture of the sodium p-styrene sulfonate homopolymer. As a result, an RNA virus infection inhibitor containing, as an RNA virus infection-inhibiting compound, the cross-linked sodium p-styrene sulfonate homopolymer was obtained. It is to be noted that the cross-linked sodium p-styrene sulfonate homopolymer was water-insoluble.

Comparative Example 1

A solution was prepared by dissolving a 2-hydroxyethyl methacrylate homopolymer (manufactured by ALDRICH, weight-average molecular weight (Mw): 300,000) in dimethyl sulfoxide at a concentration of 0.1 wt %.

Comparative Example 2

A solution was prepared by dissolving a 4-vinyl phenol homopolymer (manufactured by Maruzen Petrochemical Co., Ltd. under the trade name of "MARUKA LYNCUR M", weight-average molecular weight (Mw): 5,500) in dimethyl sulfoxide at a concentration of 0.1 wt %.

Comparative Example 3

A solution was prepared by dissolving sodium chondroitin sulfate A (manufactured by NACALAI TESQUE, Inc.) in PBS at a concentration of 1 wt %.

Comparative Example 4

A solution was prepared by dissolving sodium chondroitin sulfate C (manufactured by NACALAI TESQUE, Inc.) in PBS at a concentration of 1 wt %.

The RNA virus infection-inhibiting performance 1 of each of the RNA virus infection inhibitor solutions of Examples 1 to 8 and the solutions of Comparative Examples 1 to 4 was evaluated in the following manner, and the evaluation results are shown in Table 1.

(RNA Virus Infection-Inhibiting Performance 1)

1) Preparation of Test Samples

Each of the RNA virus infection inhibitor solutions of Examples and the solutions of Comparative Examples was diluted 10-fold, 100-fold, 1,000-fold, 10,000-fold, and 100,000-fold with a DMEM medium to prepare test samples. It is to be noted that a liquid containing only the DMEM medium used for dilution was used as a control for test sample.

2) Preparation of Virus Liquid

MDBK cells cultivated in a 10 cm-dish were inoculated with influenza virus, and were then cultivated at 37° C. for 1 hour. After the cultivation, a culture supernatant (containing naive virus) was removed. A fresh DMEM medium was added to the 10 cm-dish from which the culture supernatant had been removed, the cells were cultivated at 37° C. for 4 days, and a culture supernatant was collected and centrifuged at 800 rpm for 5 minutes to obtain a supernatant. The supernatant was 10,000-fold diluted with a DMEM medium, and the thus obtained liquid was used as a virus liquid. A liquid containing only the DMEM medium used for dilution was used as a control for virus liquid.

3) Test Method

50 µL of each of the test samples or the control for test sample and 50 µL of the virus liquid or the control for virus liquid were mixed together in combinations shown in Table 1 and reacted at room temperature for 30 minutes. Then, each of the thus obtained reaction mixtures was inoculated into MDBK cells cultivated in a 96-well microplate, and the MDBK cells were cultivated at 37° C. for 1 hour. After the cultivation, a culture supernatant (containing naive virus) was removed, a DMEM medium was added, and the MDBK cells were cultivated at 37° C. for 4 days. Then, a culture supernatant was removed, a DMEM medium containing 5 wt % of a water-soluble tetrazolium salt (produced by Dojindo Laboratories under the trade name of "WST-8") was added, and the MDBK cells were cultivated at 37° C. for 3 hours. Absorbance at 450 nm was measured using a plate reader, and viral infection-inhibiting performance was determined based on the ratio of surviving cells.

It is to be noted that the viral infection-inhibiting performance was expressed as a relative value determined when the viral infection-inhibiting performance of the reaction mixture of the control for virus liquid and the control for test sample was defined as 100 (control value). When the test sample was reacted with the virus liquid and as a result the relative value was 85 or more, the test sample was defined as "effective". When the test sample was reacted with the control for virus liquid and as a result the relative value was less than 75, the test sample was defined as "cytotoxic".

In the case of the 100,000-fold diluted test samples of Comparative Examples 1 to 3, their viral infection-inhibiting performance could not be measured due to excessive dilution.

Based on the effective concentrations and the concentrations exerting cytotoxic effects of the test samples, the range of effective dilution factors of Example 1 was 10-fold to 1000-fold, the range of effective dilution factors of Example 2 was 1000-fold to 10,000-fold, the range of effective dilution factors of Example 3 was 1,000-fold, the range of effective dilution factors of Example 4 was 100-fold to 1,000-fold, the range of effective dilution factors of Example 5 was 1000-fold, and the range of effective dilution factors of Examples 6 to 8 was 10-fold to 100-fold. Among the RNA virus infection inhibitor solutions of Examples 1 to 3, the RNA virus infection inhibitor solution of Example 2 had the strongest viral infection-inhibiting effect because it achieved the highest dilution factor.

TABLE 1

|  |  | Control for test sample | 100,000-fold | 10,000-fold | 1,000-fold | 100-fold | 10-fold |
| --- | --- | --- | --- | --- | --- | --- | --- |
| Example 1 | Virus liquid | 57 | 71 | 72 | 135 | 142 | 116 |
|  | Control for virus liquid | 100 | 101 | 107 | 106 | 94 | 105 |
| Example 2 | Virus liquid | 55 | 82 | 100 | 101 | 47 | 43 |
|  | Control for virus liquid | 100 | 110 | 114 | 83 | 60 | 43 |
| Example 3 | Virus liquid | 59 | 65 | 73 | 102 | 38 | 32 |
|  | Control for virus liquid | 100 | 102 | 103 | 78 | 49 | 32 |
| Example 4 | Virus liquid | 48 | 47 | 52 | 118 | 108 | 62 |
|  | Control for virus liquid | 100 | 109 | 102 | 109 | 86 | 70 |
| Example 5 | Virus liquid | 41 | 65 | 73 | 85 | 76 | 31 |
|  | Control for virus liquid | 100 | 110 | 123 | 115 | 67 | 35 |

TABLE 1-continued

|  |  | Control for test sample | 100,000-fold | 10,000-fold | 1,000-fold | 100-fold | 10-fold |
|---|---|---|---|---|---|---|---|
| Example 6 | Virus liquid | 43 | 46 | 47 | 52 | 85 | 106 |
|  | Control for virus liquid | 100 | 98 | 98 | 92 | 105 | 81 |
| Example 7 | Virus liquid | 40 | 42 | 42 | 45 | 100 | 120 |
|  | Control for virus liquid | 100 | 106 | 109 | 110 | 99 | 97 |
| Example 8 | Virus liquid | 51 | 53 | 54 | 83 | 98 | 88 |
|  | Control for virus liquid | 100 | 104 | 94 | 93 | 95 | 92 |
| Comparative Example 1 | Virus liquid | 69 | NT | 67 | 81 | 75 | 52 |
|  | Control for virus liquid | 100 | NT | 116 | 104 | 119 | 109 |
| Comparative Example 2 | Virus liquid | 37 | NT | 53 | 60 | 71 | 31 |
|  | Control for virus liquid | 100 | NT | 103 | 98 | 99 | 46 |
| Comparative Example 3 | Virus liquid | 51 | 56 | 48 | 52 | 46 | 42 |
|  | Control for virus liquid | 100 | 101 | 102 | 99 | 103 | 106 |
| Comparative Example 4 | Virus liquid | 37 | 46 | 54 | 48 | 53 | 48 |
|  | Control for virus liquid | 100 | 95 | 94 | 92 | 96 | 98 |

(RNA Virus Infection-Inhibiting Performance 2)

5 parts by weight of each of the RNA virus infection inhibitors obtained in Examples 9 to 13 was added to 95 parts by weight of an aerosol coating material (manufactured by Kineya Chemical K.K. under the trade name of "Cosmocolor"), and they were uniformly mixed to obtain an RNA virus infection-inhibiting coating material. 20 g of the RNA virus infection-inhibiting coating material was uniformly applied onto a polypropylene resin molded plate having an area of 1 m$^2$ and dried at room temperature for 5 hours. Then, 1.5 cm-square test pieces were cut out from the polypropylene resin molded plate. Test pieces of Comparative Example 5 were prepared in the same manner as described above except that only the aerosol coating material was used instead of the RNA virus infection-inhibiting coating material.

1) Preparation of Virus Liquid

MDBK cells cultivated in a 10 cm-dish were inoculated with influenza virus, and were then cultivated at 37° C. for 1 hour. After the cultivation, a culture supernatant (containing naive virus) was removed. A fresh DMEM medium was added to the 10 cm-dish from which the culture supernatant had been removed, the cells were cultivated at 37° C. for 4 days, and a culture supernatant was collected and centrifuged at 800 rpm for 5 minutes to obtain a supernatant. The supernatant was used as a virus liquid.

2) Test Method 0.1 mL of the virus liquid 30-fold diluted with a DMEM medium was dropped onto each of the test pieces obtained in Examples 9 to 13 and Comparative Example 5, and the test pieces were allowed to stand at room temperature for 1 minute. The virus liquid on each of the test pieces was collected and diluted 10-fold, 100-fold, 1,000-fold, and 10,000-fold with a DMEM medium. 0.1 mL per well of each of the diluted virus liquids was inoculated into MDBK cells cultivated in a 96-well microplate, and the MDBK cells were cultivated at 37° C. for 1 hour. After the cultivation, a culture supernatant (containing naive virus) was removed, and a DMEM medium was added, and the MDBK cells were cultivated at 37° C. for 4 days. Then, a culture supernatant was removed, and a DMEM medium containing 5 wt % of a water-soluble tetrazolium salt (produced by Dojindo Laboratories under the trade name of "WST-8") was added, and the MDBK cells were cultivated at 37° C. for 3 hours. Absorbance at 450 nm was measured using a plate reader, and the amount of virus that will infect 500 of cells (TCID50: Tissue Culture Infectious Dose 50) was calculated from the ratio of surviving cells to determine a virus reduction rate. The above process was performed on each of the six test pieces prepared in each of Examples and Comparative Example. The arithmetic mean of the amounts of virus (TCID50) determined from the six test pieces is defined as the "amount of virus (TCID50)" and shown in the column labeled as "TCID50 (log 10)" of Table 2. The arithmetic mean of the virus reduction rates determined from the six test pieces is defined as a "virus reduction rate" and shown in the column labeled as "reduction rate" of Table 2.

TABLE 2

|  | Thickness (μm) | Irradiation Dose (kGy) | RNA Virus Infection-Inhibiting Performance | |
|---|---|---|---|---|
|  |  |  | TCID50 (log 10) | Reduction Rate (%) |
| Example 9 | 300 | 500 | 3.71 | 81 |
| Example 10 | 600 | 500 | 3.56 | 86 |
| Example 11 | 900 | 1000 | 3.75 | 79 |
| Example 12 | 600 | 1000 | 3.83 | 75 |
| Example 13 | 600 | 2000 | 3.82 | 75 |
| Comparative Example 5 | — | — | 4.42 | 0 |

INDUSTRIAL APPLICABILITY

The RNA virus infection inhibitor according to the present invention is capable of generally inhibiting humans from being infected with viruses to prevent the occurrence of symptoms or, even when symptoms occur, to relieve the symptoms. In addition, the RNA virus infection inhibitor according to the present invention is less likely to cause unexpected discoloration or discoloration under normal service conditions, and is therefore suitable for use in various articles for daily use.

The invention claimed is:

1. An RNA virus infection inhibitor comprising an RNA virus infection-inhibiting compound comprising a copolymer of a sodium styrene sulfonate and a monomer copolymerizable therewith, and wherein the copolymer has an average molecular weight of 5,000 to 5,000,000.

2. The RNA virus infection inhibitor according to claim 1, wherein an RNA virus inhibited by the RNA virus infection inhibitor is an influenza virus.

3. The RNA virus infection inhibitor according to claim 1, which is insoluble in water.

4. The RNA virus infection inhibitor according to claim 3, which is water-insoluble and the RNA virus infection-inhibiting compound is cross-linked.

5. The RNA virus infection inhibitor according to claim 3, which is water-insoluble and the RNA virus infection-inhibiting compound is immobilized on a carrier.

6. A method for inhibition of an infection by an RNA virus comprising supplying an RNA virus infection inhibitor comprising an RNA virus infection-inhibiting compound comprising a copolymer of a sodium styrene sulfonate and a monomer copolymerizable therewith, having an average molecular weight of 5,000 to 5,000,000 to an object where an RNA virus is present, wherein the RNA virus infection inhibitor prevents cells from being infected with the RNA virus or prevents the RNA virus from growing in cells after the cells are infected with the RNA virus.

7. A method for inhibition of an infection by an RNA virus comprising previously supplying an RNA virus infection inhibitor comprising an RNA virus infection-inhibiting compound comprising a copolymer of a sodium styrene sulfonate and a monomer copolymerizable therewith, having an average molecular weight of 5,000 to 5,000,000 to an object, wherein the RNA virus infection inhibitor prevents cells from being infected with an RNA virus attached to the object after the RNA virus infection inhibitor is supplied to the object or prevents the RNA virus from growing in cells after the cells are infected with the RNA virus.

8. A method for inhibition of an infection by an RNA virus according to claim 6 or 7, wherein the RNA virus is an influenza virus.

9. An RNA virus infection-inhibiting product comprising an RNA virus target object treated with the RNA virus infection inhibitor according to claim 1.

10. The RNA virus infection-inhibiting product according to claim 9, wherein the RNA virus target object is a filter, an interior material for buildings, a fiber product, an article used inside vehicles, or an interior material for vehicles.

* * * * *